United States Patent [19]
van Regenmortel et al.

[11] Patent Number: 5,407,833
[45] Date of Patent: Apr. 18, 1995

[54] PEPTIDES OF THE SM-D ANTIGEN AND THEIR USE FOR DIAGNOSIS OF SYSTEMIC LUPUS ERYTHEMATOSUS

[75] Inventors: Marc van Regenmortel; Sylviane Muller; Jean-Paul Briand; Samira Barakat; Jean-Christophe Weber, all of Strasbourg, France

[73] Assignee: Pasteur Sanofi Diagnostics, Marnes la Coquette, France

[21] Appl. No.: 828,853

[22] PCT Filed: Jun. 6, 1991

[86] PCT No.: PCT/FR91/00445

§ 371 Date: Apr. 3, 1992

§ 102(e) Date: Apr. 3, 1992

[87] PCT Pub. No.: WO91/18920

PCT Pub. Date: Dec. 12, 1991

[30] Foreign Application Priority Data

Jun. 6, 1990 [FR] France ............... 90 07029

[51] Int. Cl.$^6$ .............. G01N 33/564; C07K 15/18; C07K 17/08
[52] U.S. Cl. .................. 436/508; 436/538; 435/7.94; 435/975; 530/325; 530/326; 530/812
[58] Field of Search ............. 436/506, 507, 508, 536, 436/538; 530/388.21, 388.2, 387.2, 326, 325, 812; 435/975

[56] References Cited

U.S. PATENT DOCUMENTS 4,629,783 12/1986 Cosand ..................... 530/324
4,784,942 11/1988 Harley ..................... 435/7.92

FOREIGN PATENT DOCUMENTS 0295719 12/1988 European Pat. Off. .
8601210 2/1986 WIPO .

OTHER PUBLICATIONS

Rokeach, L. A., et al., Proc. Natl. Acad. Sci., USA, 85(13):48321–4836, 1988.
Hubets, W. J., et al., Proc. Natl. Acad. Sci., USA, 86:4674–4678, 1989.

*Primary Examiner*—Christine M. Nucker
*Assistant Examiner*—Julie Krsek-Staples
*Attorney, Agent, or Firm*—Jacobson, Price, Holman & Stern

[57] ABSTRACT

Peptides comprising between 20 and 39 amino acids capable of reacting with antibodies against the Sm-D polypeptide. These peptides may be used in a diagnostic method to detect of antibodies against the Sm-D polypeptide in a biological sample from a person suffering from systemic lupus erythematosus.

15 Claims, 4 Drawing Sheets

PEPTIDES OF THE SM-D ANTIGEN AND THEIR USE FOR DIAGNOSIS OF SYSTEMIC LUPUS ERYTHEMATOSUS

The present invention concerns peptides capable of being recognized by antibodies present in biological fluids, in particular sera of patients or animals stricken with systemic lupus erythematosus (DLE).

The invention also concerns applications of these peptides, and compositions which contain them, to the in vitro diagnosis of systemic lupus erythematosus in humans, as well as their use in the composition of diagnostic kits.

The invention further concerns applications of these peptides in the production of immunogenic compositions and vaccination compositions against this disease.

Finally, the invention concerns antibodies which can be induced in vivo using these peptides, whether immunogenic or made immunogenic, and the application of these antibodies and the compositions containing them to in vitro diagnosis in humans stricken with DLE, as well as to the production of drugs used to fight this disease.

The presence of autoantibodies directed against cellular components is the general feature of auto-immune diseases such as systemic lupus erythematosus (DLE), scleroderma (Scl), polymyositis, and connective tissue disease (Morrow and Isenberg, 1987; Tan et al., 1988). Among the numerous kinds of autoantibodies identified for these disease, those which react with the Sm antigen constitute a very useful marker, since they are present in 20 to 30% of the subjects stricken with DLE, but are very rarely present in subjects suffering from other systemic autoimmune diseases of the connective tissues.

The Sm antigen is linked to a specific class of ribonucleoproteins, termed RNP's. These ribonucleoproteins contain five species of RNA rich in uridine, termed U1, U2, U4, US, and U6 (Lerner and Steitz, 1979; Brunel and al., 1985), in each of which seven proteins have been identified. Because of their electrophoretic mobility on polyacrylamide gels, they have been named band B' (29 Kd), band B (38 Kd), band D (16 Kd), band D' (15.5 Kd), band E (12 Kd), band F (11 Kd), and band G (9 Kd). In addition to these proteins, which make up the common nucleus, the U1-RNA particle contains three single polypeptides, corresponding, respectively, to 70 Kd, 34 Kd (A), and 22 Kd (C). The U2-RNP species contains two single polypeptides named A' (33 Kd) and B'' (28.5 Kd). The anti-RNP antibodies, or anti UI-RNP, precipitate only the constituents of the U1 particle, while the anti-Sm antibodies react with the U1, U2, U4, US, and U6 particles.

Furthermore, immunoblotting studies have demonstrated that the anti-U1-RNP antibodies react with the A, C, and 70 Kd polypeptides, while the anti-Sm antibodies react with the B', B, and D polypeptides; the E, F, and G bands are also sometimes recognized by the anti-Sm antibodies (Pettersson et al., 1984; Reichlin and Harley, 1987; Hoch, 1989; Combe et al., 1989).

Sequencing of several polypeptides of the ribonucleoproteins was obtained using recombinant DNA techniques (Theissen et al., 1986; Habets et al., 1987; Stanford et al., 1987; Sillekens et al., 1987, 1989; Yamamoto et al., 1988; Rokeach et al., 1989). European Patent Application No. 295 719 describes the cloning of a DNA coding for the Sm-D antigen (Rokeach et al., 1988). This gene codes for a polypeptide of 119 amino acids containing several basic regions; the authors believe that a glycine-arginine unit repeated nine times and localized at the C-terminal end constitutes the antigenic determinant of the Sm-D antigen. This sequence, deduced from the isolated DNA, shows little similarity with the other, aforementioned sequenced polypeptides.

European Patent Application No. 295 719 describes, moreover, a method for detecting DLE which uses the cloned Sm-D antigen.

Work carried out by Applicant on the sequence of the Sm-D polypeptide containing 119 amino acids made it possible to conclude that certain peptide sequences selected from said Sm-D polypeptide are especially advantageous for the detection of DLE. Applicant observed that certain peptides deduced from the Sm-D polypeptide are recognized in a completely specific manner by antibodies present in subjects stricken with DLE. These peptides were not recognized by antibodies present in patients afflicted with autoimmune diseases other than DLE.

These observations reveal the advantage of these peptides for the in vitro diagnosis of DLE.

FIG. 1 gives the peptide sequence of the Sm-D polypeptide. The correspondences between the amino acids and their one-letter code are as follows:

| | |
|---|---|
| A | alanine |
| C | cysteine |
| D | aspartic acid |
| E | glutamic acid |
| F | phenylalanine |
| G | glycine |
| H | histidine |
| I | isoleucine |
| K | lysine |
| L | leucine |
| M | methionine |
| N | asparagine |
| P | proline |
| Q | glutamine |
| R | arginine |
| S | serine |
| T | threonine |
| V | valine |
| W | tryptophane |
| Y | tyrosine |

The invention concerns peptides containing from 15 to 40 amino acids capable of reacting with antibodies against the Sm-D polypeptide present in a biological sample taken from a subject stricken with systemic lupus erythematosus; these peptides correspond to a portion of the sequence of the Sm-D polypeptide, or to a variant of this sequence.

Preferred peptides according to the invention comprise a part or all, or else a variant, of one of the sequences corresponding to the following formulae:

| | |
|---|---|
| XMKLVRFLMKLSHETVTIELKZ | (I) |
| XIELKNGTQVHGTITGVDVSZ | (II) |
| XDVSMNTHLKAVKMTLKNREZ | (III) |
| XKMTLKNREPVQLETLSIRGNRIRYZ | (IV) |
| XRIRYFILPDSLPLDTIRVDVEZ | (V) |
| XDTIRVDVEPKVKSKKREAVAZ | (VI) |
| XGRGRGRGRGRGRGRGRGGPRRZ | (VII). |

In the preceding formulae:

the X groups represent either a NH₂ group which is free or to which an amide is added by means of one or two alkyl groups containing from 1 to 5 carbon atoms, or a peptide group containing from 1 to 5 amino acids, in which the N-terminal amino acid itself contains an NH₂ group, whether free or incorporating an amide, as previously specified; and the Z groups represent either a free or alkoxyl OH group which thus contains an alkyl group containing from 1 to 5 carbon atoms, or a peptide group of from 1 to 5 amino acids, in which the C-terminal amino acid contains a free or alkoxyl OH group, as previously specified.

The peptide groups comprising from 1 to 5 amino acids, potentially contained in X and/or Z, are such that their presence does not fundamentally modify the immunological and, as the case arises, immunogenic properties of the peptides which lack them; however, their presence can amplify them.

Peptides preferred according to the invention include peptides matching the sequences specified in formulae (I), (II), (III), (IV), (V), (VI), and (VII), in which X represents an NH₂ group and Z, an OH group or, to the extent that the immunological properties of the peptide are not found to be modified thereby, but potentially amplified, X and Z each represent a group of from 1 to 5 amino acids.

Peptide I according to formula (I), in which X is an NH₂ group and X, a free OH group, corresponds to residues 1 to 20 of the Sm-D polypeptide illustrated in FIG. 1.

Preferred peptides corresponding to formula (I), in which Z represents a group of from 1 to 5 amino acids include peptide I, extended at its C-terminal end by the corresponding 1 to 5 amino acids in the Sm-D polypeptide in FIG. 1. Thus, Z is advantageously chosen among the following groups of from 1 to 5 amino acids: N, NG, NGT, NGTQ. NGTQV.

Peptide II, corresponding to formula (II), in which X is a free NH₂ group and X, a free OH group, corresponds to residues 17 to 35 of the Sm-D polypeptide in FIG. 1.

Preferred peptides corresponding to formula (II), in which X and Z each represent a peptide group of from 1 to 5 amino acids include peptide II, extended on either side by the corresponding 1 to 5 amino acids in the Sm-D polypeptide in FIG. 1. Thus, X is advantageously chosen from among the following groups of from 1 to 5 amino acids: T, VT, TVT, ETVT, HETVT;

and Z is advantageously selected from among the following groups of 1 to 5 amino acids: M, MN, MNT, MNTH, MNTHL.

Peptide III corresponding to formula (III), in which X is a free NH₂ group and X, a free OH group, corresponds to residues 33 to 51 of the Sm-D polypeptide in FIG. 1.

Preferred peptides corresponding to formula (III), in which X and Z each represent a group of from 1 to 5 amino acids, include peptide III, which is extended on either side by the corresponding 1 to 5 amino acids in the Sm-D polypeptide in FIG. 1. Accordingly, X is advantageously chosen from among the following groups of 1 to 5 amino acids: V, GV, TGV, ITGV, TITGV;

and Z is advantageously selected from among the following groups of 1 to 5 amino acids: P, PV, PVQ, PVQL, PVQLE.

Peptide IV corresponding to formula (IV), in which X is a free NH₂ and X, a free OH group, corresponds to residues 44 to 67 of the Sm-D polypeptide illustrated in FIG. 1.

Preferred peptides corresponding to formula (IV), in which X and Z each represent a group of 1 to 5 amino acids include peptide IV, extended on either side by the corresponding 1 to 5 amino acids in the Sm-D polypeptide in FIG. 1. Accordingly, X is advantageously chosen from among the following groups of from 1 to 5 amino acids: V, AV, KAV, LKAV, HLKAV;

and Z is advantageously selected from among the following groups of from 1 to 5 amino acids: F, FI, FIL, FILP, FILPD.

Peptide V corresponding to formula (V), in which X is a free NH₂ and X, a free OH group, corresponds to residues 64 to 84 of the Sm-D polypeptide illustrated in FIG. 1.

Preferred peptides corresponding to formula (V), in which X and Z each represent a group of 1 to 5 amino acids, include peptide V, extended on either side by the corresponding 1 to 5 amino acids in the Sm-D polypeptide in FIG. 1. Accordingly, X is advantageously chosen from among the following groups of from 1 to 5 amino acids: N, GN, RGN, IRGN, SIRGN;

and Z is advantageously selected from among the following groups of from 1 to 5 amino acids: P, PK, PKV, PKVK, PKVKS.

Peptide VI corresponding to formula (VI), in which X is a free NH₂ and X, a free OH group, corresponds to residues 77 to 96 of the Sm-D polypeptide illustrated in FIG. 1.

Preferred peptides corresponding to formula (VI), in which X and Z each represent a group of 1 to 5 amino acids, include peptide VI, extended on either side by the corresponding 1 to 5 amino acids in the Sm-D polypeptide in FIG. 1. Accordingly, X is advantageously chosen from among the following groups of from 1 to 5 amino acids: L, PL, LPL, SLPL, DSLPL;

and Z is advantageously selected from among the following groups of from 1 to 5 amino acids: G, GR, GRG, GRGR, GRGRG.

Peptide VII corresponding to formula (VII), in which X is a free NH₂ and X, a free OH group, corresponds to residues 97 to 119 of the Sm-D polypeptide illustrated in FIG. 1.

Preferred peptides corresponding to formula (VII), in which X and Z each represent a group of 1 to 5 amino acids, include peptide VII, extended at its N-terminal end by the corresponding 1 to 5 amino acids in the Sm-D polypeptide in FIG. 1. Accordingly, X is advantageously chosen from among the following groups of from 1 to 5 amino acids: A, AV, AVA, EAVA, REAVA.

The term "variants" signifies the sequences of the above-mentioned peptides which are modified by the insertion and/or deletion and/or substitution of one or several amino acids, as long as the antigenic or immunogenic properties of these sequences are not modified by said insertion, deletion, or substitution; in particular, a portion of the peptides described above may be used, to the extent that this shorter sequence preserves the immunological, and, as the case requires, immunogenic, properties as regards the antibodies reacting with the Sm-D polypeptide.

The term "variants" also signifies sequences in which the peptide bond (—CO—NH—) is replaced by the structures —CO—N(CH$_3$)—, —CH$_2$—CH$_2$, —CO—CH$_2$—, or yet again, sequences in which the peptide skeleton incorporates one or several interpolated groups, such as the groups —CH$_2$—, —NH—, and —O—. The scope of the present invention also encompasses peptides in which the amino acids containing an asymmetrical carbon are D- or L-shaped.

The invention also concerns conjugates obtained by coupling the peptides according to the invention with carrier molecules which may be physiologically acceptable and non-toxic; carrier molecules of this kind include natural proteins, such as tetanic toxoid, albumin, or albumin sera.

The peptides according to the invention possess antigenic properties and may thus be used in diagnostic procedures for case-finding or follow-up of patients stricken with DLE. Thus, the invention also concerns compositions containing the above-mentioned peptides, a mixture of these peptides, or, yet again, these peptides conjugated with a carrier molecule and capable of being recognized by the autoantibodies present in the serum or any other biological fluid of patients stricken with DLE. In vitro detection of the peptide/antibody complex is carried out by means of ELISA type immunoenzymatic, immunofluorescence, radioimmunological or radioimmunopreciptation, or immunotransfer (immunoblotting or dot-blot) tests.

To perform these tests, the invention concerns cold peptides, unlabelled or labelled with an adequate marker, which may be biotin or its derivatives, an enzyme such as peroxidase, a fluorescent marker such as fluorescein, a radioactive marker, etc.

These tests comprise the following steps, for example:
 deposition of a determinate quantity of a composition containing a peptide, or a conjugate of a peptide according to the invention, in the wells of a microtitration plate or other support, such as balls or nitrocellulose diaphragms, for example;
 deposition in the wells of the biological fluid to be tested, or incubation of this fluid when using balls or a diaphragm, in the presence of saturating agents or following preliminary saturation of the activated supports; and
 after incubation and washing of the microplates or balls, deposition in the wells, or incubation when using balls, of a system for revealing the peptide/antibody complex which may have been formed.

In another embodiment of this type of test, use is made of a peptide mixture which recognizes, first, antibodies present in the sera of patients stricken with DLE, and second, antibodies present in sera of patients afflicted with another autoimmune disease.

The invention further concerns the antibodies formed to combat the peptides according to the invention; these antibodies may be polyclonal or monoclonal and are produced using any hybridoma prepared according to conventional cellular fusion techniques uniting splenic cells, whether activated in vitro by the antigen or collected from an animal immunized against one of the peptides according to the invention, and cells from a myelomatous cell strain.

Because of the specificity of the peptides according to the invention for the antibodies of patients stricken with DLE, the antibodies prepared using these peptides constitute probes which are also very specific for the Sm-D antigen of DLE.

Furthermore, the antibodies formed against the peptides of the invention and the autoantibodies of patients reacting with said peptides and obtained after affinity chromatography may be used to prepare anti-idiotype antibodies which form, in part, an exact copy of the original antigenic peptide and which are thus capable of bonding to the autoantibodies observed in patients stricken with DLE.

The present invention thus concerns these anti-idiotype antibodies and compositions which contain them, as well as their application for the in vitro diagnosis in humans of the presence of autoantibodies observed in cases of DLE.

Finally, the invention concerns immunogenic compositions for the production of vaccines whose active constituent is formed by at least one peptide or anti-idiotype antibody according to the invention, potentially conjugated with a carrier molecule and inducing the production of antibodies against said peptides, these compositions being capable of interfering with the pathology and/or the clinical manifestations of DLE. The pharmaceutical compositions according to the invention which can be used as vaccines include solutions or suspensions which can be injected or administered by other routes and which can be administered in doses of between 10 µg/kg and 100 mg/Kg of the peptide according to the invention.

Other features and advantages of the invention will emerge from a reading of the following examples, illustrated by the attached figures. It is obvious that these examples cannot be interpreted as tending to restrict the scope of the claims.

EXAMPLE 1

SYNTHESIS, PURIFICATION, AND CHARACTERIZATION OF THE PEPTIDES

The peptides according to the invention can be prepared using conventional peptide-synthesis techniques in the solid phase, either by successive condensation of the amino acid residues in the required order, or by condensation of the amino acid residues on a preliminarily-formed fragment which already contains several amino acids in the appropriate order, or, yet again, by condensation of several preliminarily-prepared fragments, while taking care to preliminarily protect all of the reactive functions carried by the amino acid residues or fragments, except for the amine and carboxyl functions which take part in the peptide bond formed during condensation.

According to a preferred method of preparation of the peptides according to the invention, a PAM resin was used. The amine function of the added amino acid was protected by a terbutyloxycarbonyl group (Boc) and the lateral chains of the trifunctional amino acids were protected, for example, by the following groups: cyclohexyl for glutamic and aspartic acid, benzyl for threonine and serine, 2-chlorobenztloxycarbonyl for lysine, 2,6-dichlorobenzyl for tyrosine, and p-toluenesulfonyl for arginine and histidine. Methionine was added as terbutyloxycarbonyl (O) methioninesulfoxide, which was reduced to methionine during final cleavage of the resin peptide under the effect of the anhydrous fluorhydric acid. The amino acids Bocs were coupled in the form of a benzotriazole ester, except for the histidine Boc, which was added in a symmetrical anhydrous form.

Total coupling time was approximately 45 minutes. A ninhydrin test was carried out to check the proper formation of the coupling which, if necessary, can be doubled.

After synthesis and the final deprotection step, the resin was washed and dried. Depending on the presence or absence of (O)methionine in the sequence, a strong or weak treatment using fluorhydric acid was used for deprotection and to perform the cleavage of the resin peptide.

After lyophilization, the crude product was dissolved in 10% acetic acid and purified by medium-pressure chromatography. Peptides were then characterized by high-pressure chromatography in the liquid phase, and by analysis of their amino acid composition using mass spectometry.

EXAMPLE 2

SEROLOGIC STUDIES

1—Materials a. 165 patients stricken with active systemic lupus erythematosus (DLE) were tested and compared to 32 patients suffering from scleroderma (Scl), 14 patients stricken with mixed connective tissue disease, 2 stricken with polymyositis, 13 patients suffering from sarcoidosis, 5 patients stricken with Sjogren's syndrome, 35 persons stricken with rheumatoid arthritis, and 86 patients suffering from juvenile chronic arthritis.

b. 53 sera taken from healthy volunteers were used as controls.

c. 18 human sera and 5 mice monoclonal antibodies which recognize the bands of the Sm antigen by immunoblotting were used. These five antibodies were taken, respectively, from the H126 clone (described by Reuter and Luhrmann in 1986) which reacts with bands B' B and D from the Y12 clone (described by Pettersson et al., in 1984) reacting with bands B', B, D and E, from the H57 clone (described by R. Luhrmann) which reacts with bands B1 and B, and from clones 2-73 (anti-U1 RNP) and 7-13 (anti-Sm) (described by Billings et al. in 1982 and 1985), which bind the D polypeptide.

d. Peptides I, II, III, IV, V, VI, and VII were synthesized using the technique described in Example 1. Their purity degree was at least 85%.

2. Method

The immunological reaction between peptides I, II, III, IV, V, VI, and VII and the antibodies of the various sera was measured by means of ELISA in accordance with the following protocol:

1 to 2 µM of each peptide, diluted in an 0.05M carbonate buffer solution having a pH of 9.6, were deposited in the wells of a microtitration plate at a temperature of 37° Celsius. The plates were then incubated for 1 hour at 37° Celsius with a bovine albumin serum, in a concentration of 10 mg/ml, in a PBS buffer, pH=7.4 containing 0.055 of Tween 20 (PBS-T-BSA);

after three washings in the PBS-T buffer, the patient's serum, diluted to 1/1000 in the PBS-T-BSA buffer, was added to the wells and allowed to incubate for 1 hour at 37° Celsius;

after several washings, the reaction was detected by successive one-hour incubations at 37° Celsius with a biotin conjugate specific for human IgG, then with a streptavidine conjugate labelled with peroxidase, also for one hour at 37° Celsius.

Detection of the enzymatic reaction was effected by adding a peroxidase substrate, such as 2,2'-azinobis(3-ethylbenzthiazoline sulfonate) (ABTS) for one hour at 37° Celsius. The optical density value was measured with a spectrophotometer at 405 nm. Detection may also take place in a single step after incubation of the serum, by adding an anti-human IgG conjugate labelled with peroxidase (30 mn at 37° Celsius), then the substrate (TMB 3,3',5' tetramethylbenzidine) for 15 mn at 37° Celsius. The reaction was blocked by adding 2 m HCl, and the optical density was read at 450 nm.

In order to determine the positivity threshold of the test, a series of 53 sera taken from healthy individuals, diluted to 1/1000, were tested with 1 µM and 2 µM of peptides I and IV, which were placed in the wells of the microplates. Average absorption at 405 nm was 0.10, with a standard deviation of 0.084. Accordingly, a serum was considered positive when its optical density value was greater than the average increased by twice the standard deviation, i.e., 0.3 unit of optical density.

Figure 2A:
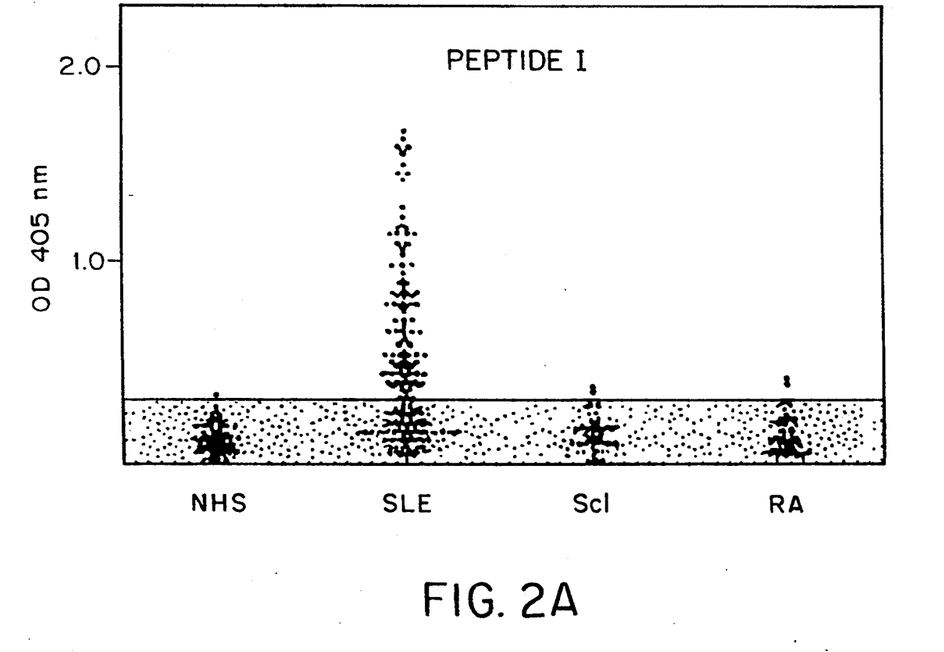
Figure 2B:
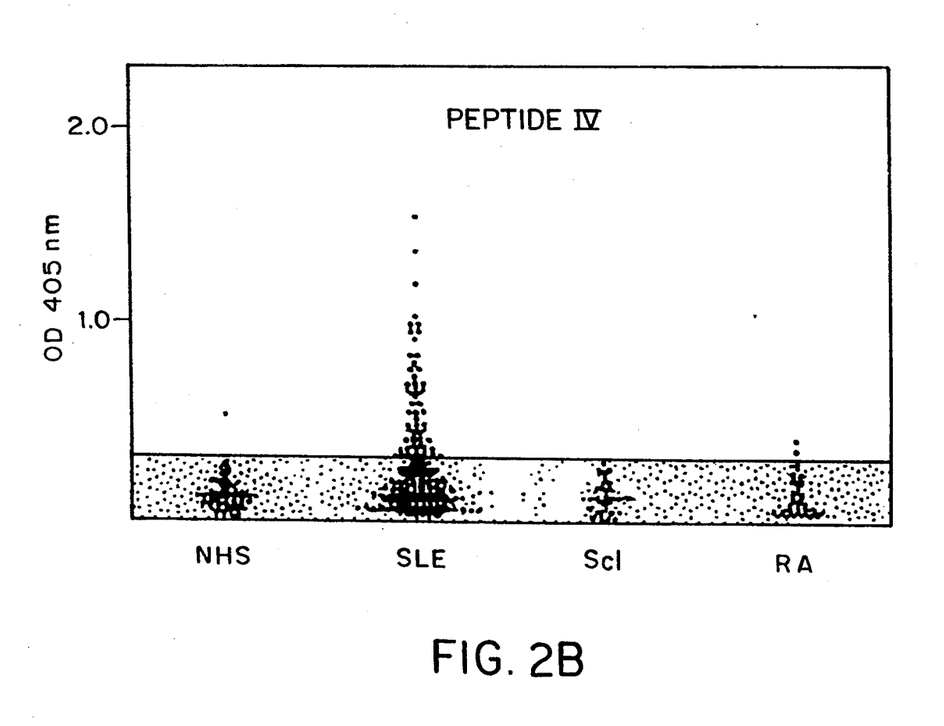
Figure 3A:
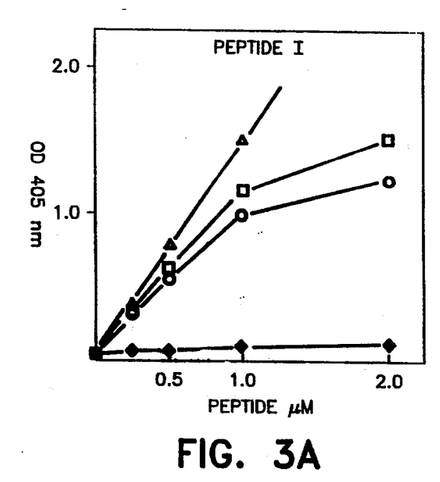
Figure 3B:
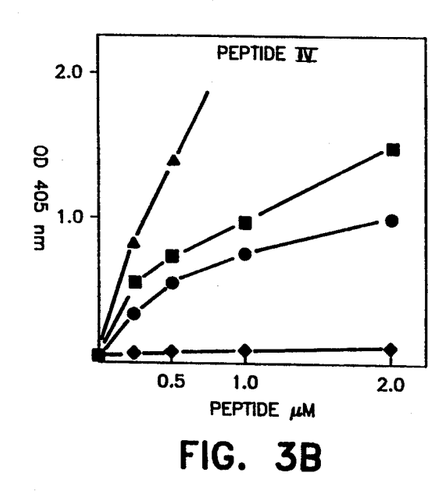
Figure 3C:
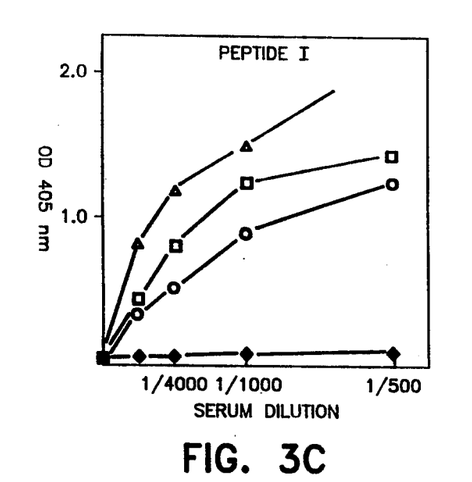
Figure 3D:
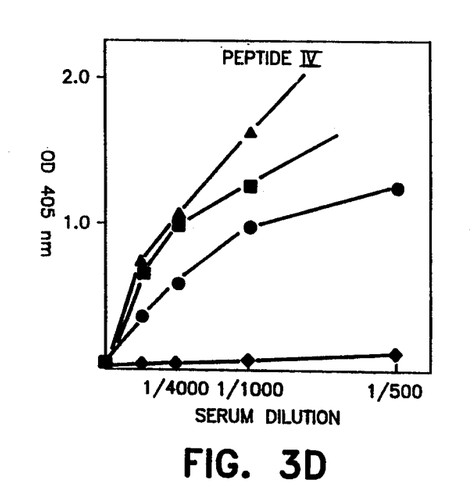

By using this threshold, 1.8% of the sera taken from normal individuals was found to be positive using the two peptides (FIG. 2). By setting the threshold at the average optical density plus 5 standard deviations, the test became completely specific for DLE.

3. Studies of 18 patient sera which recognized the D band by immunoblotting

Among these sera, 12, or 67%, reacted with peptide I (optical density of between 0.30 and 0.81; average value of the optical density was 0.47, and the value of the standard deviation was 0.15); 16, or 89%, reacted with peptide IV (optical density of between 0.30 and 1.20; average optical density value was 0.57; and standard deviation value was 0.25); and 6, or 33%, reacted with peptide VII (optical density of between 0.30 and 0.73; average optical density value was 0.46; and the standard deviation was 0.16).

All of the sera which reacted with peptide I and/or peptide VII also reacted with peptide IV. None of the sera reacted with peptides II, III, V, VI.

It appears, therefore, that most of the sera reacting by immunoblotting with band D can be identified by their reaction in ELISA with peptide IV alone.

Furthermore, the five mice monoclonal antibodies reacting by immunoblotting with some bands of the Sm antigen were tested with peptides I, II, III, IV, V, VI, and VII.

The antibodies of clones 2-73 and 7-13 reacted with peptide VII in ELISA. The three other antibodies did not react with any of the seven peptides.

4. Study of sera taken from patients stricken with DLE and other rheumatic diseases Among the 165 patient suffering from DLE, 59% had antibodies which could react with peptide I (optical density of between 0.30 and 1.67; average optical density value: 0.77); 37% of these patients had antibodies which reacted with peptide IV (optical density of between 0.30 and 0.58; average optical density: 0.58); two sera other than the 165 tested reacted with peptide VII; and no serum reacted with peptides II, III, V, and VI (FIG. 2, Table I).

Peptides I and IV were rarely recognized by the antibodies in the sera of patients stricken with a rheumatic disease other than DLE. 6% of the sera of patients stricken reacted with either of two peptides, i.e., peptide I (optical density of between 0.30 and 0.39) or peptide IV (optical density of between 0.30 and 0.41). Only 6% of the sera from patients stricken with scleroderma reacted with peptide I (optical density of between 0.30 and 0.36), and none with peptide IV.

The results given by peptides I and IV are tabulated in Table I below. Patient sera were diluted to 1/1000 and placed in contact with 1 μM of peptide I and 2 μM of peptide IV, adsorbed on a microtitration plate. Values were expressed as a percentage of positive sera out of the total number of sera tested. A serum is considered positive when the optical density value is greater than, or equal to, 0.3 (a value corresponding to the average optical density value for the 53 sera taken from healthy individuals increased by twice the standard deviation), after a one-hour incubation of the human anti-IgG conjugated with the enzyme, with the substrate of this enzyme.

TABLE I

| type of serum | number of sera | peptide I | peptide IV |
|---|---|---|---|
| DLE | 165 | 58.8% | 37.0% |
| Scleroderma | 32 | 6.3% | 0 |
| Mixed connective tissue disease | 14 | 0 | 0 |
| Polymyositis | 2 | 0 | 0 |
| Sarcoidosis | 13 | 0 | 0 |
| Sjogren's syndrome | 5 | 0 | 0 |
| Rheumatoid arthritis | 35 | 5.7 | 5.7 |
| Juvenile chronic arthritis | 86 | 1.2 | 1.2 |
| Normal | 53 | 1.8 | 1.8 |

The results are also presented in different form in FIG. 2, appended.

To the extent that all of the sera showing positive with peptide IV were also positive with peptide I in ELISA, the use of peptide I in ELISA allowed identification of approximately 60% of the sera of patients stricken with systemic lupus erythematosus. FIG. 3, appended, shows the connection of the autoantibodies present in the serum of patients stricken with DLE with peptides I and IV.

EXAMPLE 3

PREPARATION AND STUDY OF RABBIT ANTISERA

1. Preparation of antisera

Antisera against peptides I, II, III. IV, V, VI, and VII were obtained from rabbits. At each injection, the rabbit received 100 μg of the peptide in a saline solution in the presence of Freund's adjuvant. Series of subcutaneous injections were administered twice monthly for four months, and two rabbits were used for each peptide.

After three injections, blood samples were regularly taken from the rabbits after each injection, and the proportion of serous antibodies was measured in ELISA.

2. Method

Bonding of the rabbit antibodies with the seven peptides was measured using ELISA, according to a method identical to that described above (see Example II, point 2), except as regards the immunological reaction, which was disclosed by adding rabbit anti-gammaglobulins prepared in goats and conjugated with peroxidase.

Furthermore, to test the monoclonal antibodies, the supernatants in hybridoma cultures were diluted to 1/50 in a PBS-T-BSA buffer and placed in contact with the peptides. The reaction was disclosed by successive additions of mice anti-gammaglobulins prepared in rabbits and rabbit anti-gammaglobulins prepared in goats and conjugated to peroxidase, as previously described.

3. Results

A strong response was obtained for peptides I, II, III, IV, V, and VI after three injections of the rabbits (the optical density at 405 nm was greater than 2.0 after 60 minutes of incubation of the substrate, the antisera being diluted to 1/5000 and 1/10000.

These results indicate that the inability of peptides II, III, V, and VI to react with the patient sera (see Table I, above) was not the result of insufficient adsorption of these peptides on the ELISA plate. Only peptide VII gave a more moderate response in rabbits (the optical density value was 2.0 after 60 minutes of incubation with sera diluted to 1/250 and 1/500). This relatively low level of reactivity of the antiserum with peptide VII was not due to poor adsorption of the peptide on the ELISA plate, since the monoclonal antibodies 2–73 and 7–13 reacted strongly with this peptide (see Example II, point 3).

EXAMPLE IV

STUDY OF THE CORRELATION BETWEEN ANTI-DNA DLE ANTIBODIES AND ANTIBODIES AGAINST THE PEPTIDES OF THE D POLYPEPTIDE

The sera of patients suffering from DLE were also tested to determine the presence of antibodies which, in ELISA, reacted with native double-stranded DNA. No correlation was found between the presence of anti-DNA antibodies and the presence of antibodies reacting with peptides I or IV.

EXAMPLE V

PREDICTION OF THE ANTIGENIC SITES OF THE Sm-D ANTIGEN

The method implemented used algorithms based on certain parameters, such as the hydrophilia and mobility of short segments of the primary structure of proteins (Van Regenmortel and Daney de Marcillac, 1988).

Figure 4A:
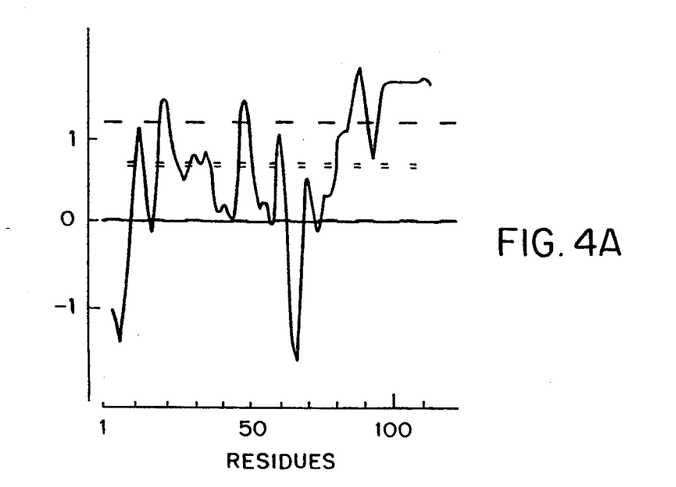
Figure 4B:
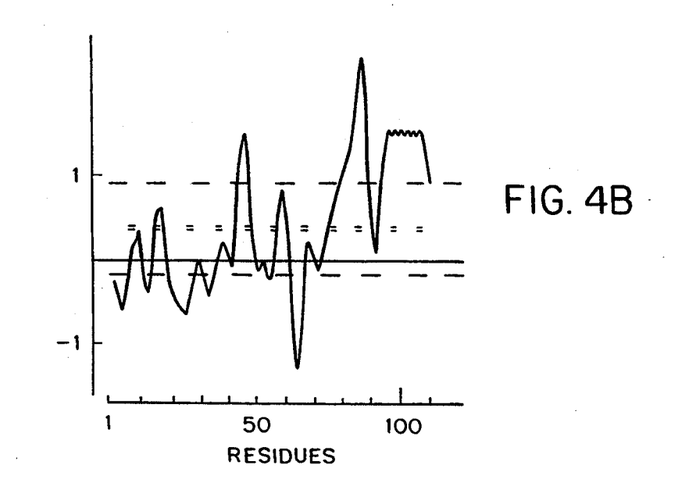
Figure 4C:
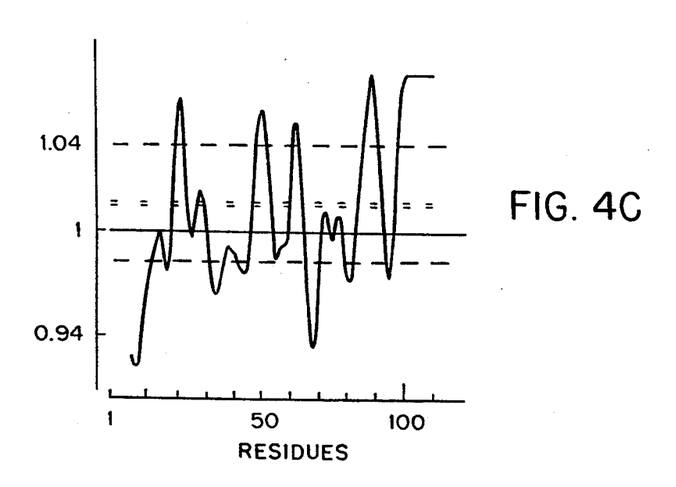

Surprisingly, the results obtained did not indicate that peptide I, extending from residues 1 to 20 of the Sm-D polypeptide, contained an epitope determinant of the polypeptide. These results are given in FIG. 4.

The legends for the figures illustrating the foregoing description are as follows:

BRIEF DESCRIPTION OF THE DRAWINGS

FIG. 1 represents the sequence deduced from the Sm-D polypeptide in accordance with the c-DNA.

FIG. 2 represents the bond of peptides I and IV in ELISA. Activity of the anti-peptide IgG's was measured for 53 sera taken from health subjects (NHS), 165 sera from patients stricken with systemic lupus erythematosus, 32 sera from patients suffering from scleroderma, and 35 sera from patients suffering from rheumatoid arthritis. All sera were diluted to 1/1000, and the antibody level was expressed in units of optical density at 405 nm, after hydrolysis of the substrate for 60 minutes.

FIG. 3 represents, in ELISA, the bond between six sera from patients stricken with systemic lupus erythematosus (l=Δ, n=□, s=, m=  , r=  , and s= and one serum from a healthy subject (u=  ) with peptide I (frames A and C) and peptide IV (frames B and D). In A and B, the sera were diluted to 1/1000 and placed in contact with various concentrations of peptide I. In B and D, various concentrations of the sera were placed in contact with 1 and 2 μM of peptides I and IV, respectively.

FIG. 4 represents the antigenic prediction profiles of the Sm-D polypeptide, constructed using the following scales:
* A: according to Parker et al. (1986)
* B: accord to Hopp and Wood (1981)
* C: according to Karplus and Schultz (1985).

These scales were standardized in accordance with Van Regenmortel and Daney de Marcillac (1988). The diagrams are drawn between the fourth residue and residue n-3. The epitopes recognized by the antibodies of patients suffering from DLE are shown in thick lines.

All of the results mentioned in the preceding examples clearly indicate that the peptides deduced from the Sm-D antigen are particularly useful in the implementation of a quantitative diagnostic test of pronounced sensitivity to DLE.

The observations collected concerning peptide I show that 59% of patients suffering from DLE possessed IgG-type antibodies which recognized the peptide, while 6% of sera of patients stricken with another autoimmune disease and less than 4% of sera taken from normal subjects reacted with peptide I in ELISA. Peptide I, potentially used with peptide IV, thus constitutes a particularly effective probe for diagnosis of disseminated lupus erythematosus.

This percentage of nearly 60% was greater than that previously described using purified proteins.

REFERENCES

Billings, P. B., Allen, R. W., Jensen, F. C., and Hoch, S. O., 1982. "Anti-RNP Monoclonal Antibodies Derived from a Mouse Strain with Lupus-Like Autoimmunity, *J. Immunol.*, 128:1176.

Billings, P. B., Barton, J. R., and Hoch, S. O., 1985. "A Murine Monoclonal Antibody Recognizes the 13,000 Molecular Weight Polypeptide of the Sm Small Nuclear Ribonucleoprotein Complex, *J. Immunol.*, 135:428.

Bringmann, P., and Luhrmann, R., 1986. "Purification of the Individual snRNPs U1, U2, U5, and U4/U6 from HeLa Cells and Characterization of their Protein Constituents. *The Embo J.*, 5:3509.

Brunel, C., Sri-Widada, J., and Jeanteur, P., 1985. "sn RNP's and scRNP's in Eukaryotic Cells." In *Progr. Mol. Subcell. Biol.*, Vol. 9, F. E. Hahn, D. J. Kopecko, W. E. G. Muller, eds., Springer Verlag (Berlin), p. 1–52.

Combe, B., Rucheton, M., Graafland, H., Lussiez, V., Brunel, C., and Sany J., 1989. "Clinical Significance of Anti-RNP and Anti-Sm Autoantibodies as Determined by Immunoblotting and Immunoprecipitation in Sera from Patients with Connective Tissue Diseases." *Clin. Exp. Immunol.*, 75:18.

Eisenberg, R. A., Dyer, K., Craven, S. Y., Fuller, C. R., and Yount, W. J., 1985. "Subclass Restriction and Polyclonality of the Systemic Lupus Erythematosus Marker Antibody anti-Sm. *J. Clin. Invest.* 75:1270.

Habets, W. J., Sillekens, P. T. G., Hoet, M. H., Schaiken, J. A., Roebroek, A. J. M., Leunissen, J. A. M, Van de Ven, W. J. M, and Van Venrooij, W. J., 1987. "Analysis of a cDNA Clone Expressing a Human Autoimmune Antigen: Full-Length Sequence of the U2 Small Nuclear RNA-Associated B" Antigen. *Proc. Natl. Acad. Sci. U.S.A.* 84:2421.

Hardin, J. A., 1986. "The Lupus Autoantigens and the Pathogenesis of Systemic Lupus Erythematosus. *Arthritis Rheum.* 29:457.

Hoch, S. O., 1989. "Application of Protein Blotting to the Study of Autoimmune Disease." In *Protein Blotting Methodology, Research, and Diagnostic Applications.* B. A. Baldo, E. R. Toveym S. Karger AG, Basel, p. 140–164.

Hopp, T. P. and Woods, K. R., 1981. "Prediction of Protein Antigenic Determinants from Amino Acid Sequences." *Proc. Natl. Acad, Sci. U.S.A.* 78:3824.

Kaiser, E., Colescott, R. L., Bossinger, C. D., and Cook, P. I., 1970. "Color Test for Detection of Free Terminal Amino Groups in the Solid Phase Synthesis of Peptides. *Anal. Biochem.*, 34:595.

Karplus, P. A., and Schulz, G. E., 1985. "Prediction of Chain Flexibility in Proteins. *Naturwissenschaften* 72:212.

Lerner, M. R., and Steitz, J. A., 1979. "Antibodies to Small Nuclear RNA's Complexed with Proteins Are Produced by Patients with Systemic Lupus Erythematosus. *Proc. Natl. Acad. Sci. U.S.A.*, 76:5495.

McCarty, G. A., Rice, J. R., Bembe, M. L., and Pisetsky, D. S., 1982. "Independent Expression of Autoantibodies in Systemic Lupus Erythematosus. *J. Rheum.*, 9:691.

Merrifield, R. B., 1963. "Solid Phase Peptide Synthesis. I. The Synthesis of a Tetrapeptide. *J, Amer. Chem Soc.*,85:2149.

Morrow, J. and Isenberg, D. A., 1987. "Systemic Lupus Erythematosus." In *Autoimmune Rheumatic Diseases*, Chapter 3, Blackwell Scientific Publications, p. 48.

Muller, S., Plaué, S., Couppez, M., and Van Regenmortel, M. H. V., 1986. "Comparison of Different Methods for Localizing Antigenic Regions in Histone H2A. *Molec. Immunol.*, 23:593.

Muller, S., Bonnier, D., Thiry, M. and Van Regenmortel, M. H. V., 1989. "Reactivity in Systemic Lupus Erythematosus with Synthetic Core Histone Peptides. *Int. Arch, Allergy Appl. Immunol.*, 89:288.

Muller, S., Briand, J. P., and Van Regenmortel, 1988. "Presence of Antibodies to Ubiquitin During the Autoimmune Response Associated with Systemic Lupus Erythematosus. *Proc. Natl. Acad. Sci. U.S.A.* 85:8176.

Parker, J. M. R., Guo, D., and Hodges, R. S., 1986. "New Hydrophilicity Scale Derived from High-Performance Liquid Chromatography Peptide Retention Data: Correlation of Predicted Surfaces Residues with Antigenicity and X-Ray-Derived Accessible Sites. *Biochemistry*, 25:5425.

Pettersson, I, Hinterberger M, Mimori, T., Gottlieb, E., and Steitz, J. A., 1984. "The Structure of Mammalian Small Nuclear Ribonucleoproteins. *J. Biol. Chem.*, 259:5907.

Plaué, S. and Briand, J. P., 1988. "Solid-Phase Peptide Synthesis. In *Synthetic Polypeptides as Antigens* in the series *Laboratory Techniques in Biochemistry and Molecular Biology*, Vol. 19, R. H. Burdon and P. H. Van Knippenberg, ed.s, Elsevier, Amsterdam, pp. 41–94.

Plaué, S., Muller, S., and Van Regenmortel, M. H. V., 1989. "A Branched, Synthetic Octapeptide of Ubiquinated Histone H2A as a Target of Autoantibodies. *J. Exp. Med.*, 169:1607.

Reichlin, M. and Harley, J. B., 1987. "ANA Subsets in Systemic Lupus Erythematosus." In *Systemic Lupus Erythematosus.* J. S. Smolen, C. C. Zielinski, eds., Springer Verlag (Berlin, pp. 105–123.

Reuter, R. and Luhrmann, R. 1986. "Immunization of Mice with Purified U1 Small Nuclear Ribonucleoprotein (RNP) Induces a Pattern of Antibodies Specificities Characteristic of the anti-Sm and anti-RNP Autoimmune Response of Patients with Lupus Erythematosus, As Measured by Monoclonal Antibodies. *Proc. Natl. Acad. Sci. U.S.A.*, 83:8689.

Rokeach, L. A., Haselby, J. A., and Hock, S. O., 1988. "Molecular Cloning of a cDNA Encoding the Human Sm-D Autoantigen." *Proc. Natl. Acad. Sci. U.S.A.*, 85:4832.

Rokeach, L. A., Jannatipour, M., Haselby, J. A., and Hoch, S. O., 1989. "Primary Structure of a Human Small Nuclear Ribonucleoprotein Polypeptide as Deduced by cDNA Analysis." *J. Biol. Chem.*, 264:5024.

Sillekens, P. T. G., Habets, W. J., Beijer, R. P., and Van Venrooij, W. J., 1987. "CDNA Cloning of the Human U1 snRNA-Associated A Protein: Extensive Homology Between U1 and U2 snRNP-Specific Proteins. *The Embo J.*, 6:3841.

Sillekens, P. T. G., Beijer, R. P., Habets, W. J., and Van Venrooij, W. J., 1989. "Molecular Cloning of the cDNA for the Human U2 snRNA-Specific A' Protein. *Nucl. Acids Res.*, 17:1893.

Stanford, D. R., Rohleder, A., Neiwanger, K., and Wieben, E. D., 1987. "DNA Sequence of a Human Sm Autoimmune Antigen. *J. Bio. Chem.*, 262:9931.

Tam, J. P., Heath, W. F., and Merrifield, R. B., 1983. "SN2 Deprotection of Synthetic Peptides with a Low Concentration of HF in Dimethyl Sulfide: Evidence and Application in Peptide Synthesis. *J. Amer. Chem, Soc.*, 105: 6442.

Tan, E. M., Chan, E. K. L, Sullivan, K. F., and Rubin, R. L., 1988. "Antinuclear Antibodies (ANA's): Diagnostically Specific Immune Markers and Clues Toward the Understanding of Systemic Autoimmunity. *Clin. Immunol. Immunopath.*, 47:121.

Tan, E. M. and Kunkel, H. G., 1966. "Characteristics of a Soluble Nuclear Antigen Precipitating With Sera of Patients with System Lupus Erythematosus." *J. Immunol.*, 96:464.

Theissen, H., Etzerodt, M., Reuter, R., Schneider, C., Lottspeich, F., Argos, P., Luhrmann, R., and Philipson, L., 1986. "Cloning of the Human cDNA for the U1 RNA-Associated 70K Protein. *The EMBO J.* 5:3209.

Tuaillon, N., Muller, S., Pasquali, J. L., Bordigoni, P., Youinou, P., and Van Regenmortel, M. H. V., 1990. "Antibodies from Patients With Rheumatoid Arthritis and Juvenile Chronic Arthritis Analyzed With Core Histone Synthetic Peptides. *Int. Arch. All. Appl. Immunol.* (in press).

van Regenmortel, M. H. V. and Daney de Marcillac, G., 1988. "An Assessment of Prediction Methods for Locating Continuous Epitopes in Proteins. *Immunol. Lett.*, 17: 95.

Williams, D. G., Charles, P. J., and Maini, R. N., 1988. "Preparative Isolation of p67, A, B, B' and D from nRNP/Sm and Sm Antigens by Reverse-Phase Chromatography. *J. Immunol. Meth.*, 113:25.

Yamamoto, K., Miura, H., Moroi, Y., Yoshinoya, S., Goto, M., and Nishioka, K., and Miyamoto, T., 1988. "Isolation and Characterization of a Complementary DNA Expressing Human U1 Small Nuclear Ribonucleoprotein C Polypeptide. *J. Immunol.*, 140:311.

---

We claim:

1. Peptide capable of reacting with antibodies against the Sm-D polypeptide present in a biological sample taken from a subject stricken with systemic lupus erythematosus, wherein said peptide is selected from the group consisting of (i) a peptide comprising a sequence corresponding to the following formula:

XMKLVRFLMKLSHETVTIELKZ         (I)

in which X represents a free $NH_2$ group and Z represents either a free OH group or a peptide group chosen from among the following groups of 1 to 5 amino acids: N, NG, NGT, NGTQ, NGTQV; and (ii) a peptide comprising the sequence corresponding to the following formula:

XKMTLKNREPVQLETLSIRGNRIRYZ     (IV)

in which X represents either a free $NH_2$ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD.

2. Antigenic composition comprising a peptide according to claim 1, wherein said composition reacts immunologically with the autoantibodies present in biological fluids of patients suffering from systemic lupus erythematosus.

3. Antigenic composition comprising a peptide according to claim 1, wherein said composition reacts immunologically with the autoantibodies present in sera of patients suffering from systemic lupus erythematosus.

4. Peptide according to claim 1 comprising a sequence corresponding to the following formula:

XMKLVRFLMKLSHETVTIELKZ         (I)

in which X represents a free $NH_2$ group and Z represents either a free OH group or a peptide group chosen from among the following groups of 1 to 5 amino acids: N, NG, NGT, NGTQ, NGTQV.

5. Antigenic composition comprising a peptide according to claim 4, wherein said composition reacts immunologically with the autoantibodies present in biological fluids of patients suffering from systemic lupus erythematosus.

6. Antigenic composition comprising a peptide according to claim 4, wherein said composition reacts immunologically with the autoantibodies present in sera of patients suffering from systemic lupus erythematosus.

7. Peptide according to claim 1 comprising a sequence corresponding to the following formula:

XKMTLKNREPVQLETLSIRGNRIRYZ     (IV)

in which X represents either a free $NH_2$ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD.

8. Antigenic composition comprising a peptide according to claim 7, wherein said composition reacts immunologically with the autoantibodies present in biological fluids of patients suffering from systemic lupus erythematosus.

9. Antigenic composition comprising a peptide according to claim 7, wherein said composition reacts immunologically with the autoantibodies present in sera of patients suffering from systemic lupus erythematosus.

10. In vitro diagnostic procedure for detecting autoantibodies to systemic lupus erythematosus in a biological fluid, wherein said procedure comprises the steps of:

placing said biological fluid in contact with at least one peptide selected from the group consisting of:
(i) a peptide comprising a sequence corresponding to the following formula:

XMKLVRFLMKLSHETVTIELKZ         (I)

in which X represents a free $NH_2$ group and Z represents either a free OH group or a peptide group chosen from among the following groups of 1 to 5 amino acids: N, NG, NGT, NGTQ, NGTQV; and (ii) a peptide comprising the sequence corresponding to the following formula:

XKMTLKNREPVQLETLSIRGNRIRYZ     (IV)

in which X represents either a free $NH_2$ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD;

or a conjugate of the peptide with a carrier molecule, under conditions allowing the formation of an immunological complex between the peptide or conjugate and the antibodies that may be present in the fluid; and detecting, in the biological fluid the presence or absence of the immunological complex using physical or chemical methods.

11. Procedure of claim 10 wherein the peptide comprises the sequence corresponding to the following formula:

XMKLVRFLMKLSHETVTIELKZ         (I)

in which X represents a free $NH_2$ group and Z represents either a free OH group or a peptide group chosen from among the following groups of 1 to 5 amino acids: N, NG, NGT, NGTQ, NGTQV.

12. Procedure of claim 10 wherein the peptide comprises the sequence corresponding to the following formula:

XKMTLKNREPVQLETLSIRGNRIRYZ (IV)

in which X represents either a free NH₂ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD.

13. Kit for the in vitro diagnosis of systemic lupus erythematosus comprising:

at least one peptide selected from the group consisting of (i) a peptide comprising a sequence corresponding to the following formula:

XMKLVRFLMKLSHETVTIELKZ (I)

in which X represents a free NH₂ group and Z represents either a free OH group or a peptide group chosen from among the following groups of 1 to 5 amino acids: N, NG, NGT, NGTQ, NGTQV; and (ii) a peptide comprising the sequence corresponding to the following formula:

XKMTLKNREPVQLETLSIRGNRIRYZ (IV)

in which X represents either a free NH₂ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD; or a conjugate of the peptide with a carrier molecule;

reagents that, when combined, provide a medium which promotes immunological complex formation between the peptide or conjugate and autoantibodies which may be present in a biological sample;

at least one reagent capable of detecting the immunological complex; and a standard.

14. Kit of claim 13 wherein the peptide comprises the sequence corresponding to the following formula:

XMKLVRFLMKLSHETVTIELKZ (I)

in which X represents a free NH₂ group and Z represents either a free OH group or a peptide group chosen from among the following groups of 1 to 5 amino acids: N, NG, NGT, NGTQ, NGTQV.

15. Kit of claim 13 wherein the peptide comprises the sequence corresponding to the following formula:

XKMTLKNREPVQLETLSIRGNRIRYZ (IV)

in which X represents either a free NH₂ group or a peptide group chosen from among the following groups of from 1 to 5 amino acids: V, AV, KAV, LKAV, HKLAV; and Z represents either a free OH group or a peptide group chosen from among the following groups of from 1 to 5 amino acids: F, FI, FIL, FILP, FILPD.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Homo sapiens     ( x i ) SEQUENCE DESCRIPTION: SEQ ID NO:1:

```
Met  Lys  Leu  Val  Arg  Phe  Leu  Met  Lys  Leu  Ser  His  Glu  Thr  Val  Thr
  1              5                        10                       15

Ile  Glu  Leu  Lys  Asn  Gly  Thr  Gln  Val  His  Gly  Thr  Ile  Thr  Gly  Val
              20                        25                       30

Asp  Val  Ser  Met  Asn  Thr  His  Leu  Lys  Ala  Val  Lys  Met  Thr  Leu  Lys
              35                        40                       45

Asn  Arg  Glu  Pro  Val  Gln  Leu  Glu  Thr  Leu  Ser  Ile  Arg  Gly  Asn  Arg
         50                        55                       60

Ile  Arg  Tyr  Phe  Ile  Leu  Pro  Asp  Ser  Leu  Pro  Leu  Asp  Thr  Ile  Arg
 65                        70                       75                       80

Val  Asp  Val  Glu  Pro  Lys  Val  Lys  Ser  Lys  Lys  Arg  Glu  Ala  Val  Ala
              85                        90                       95
```

Gly Arg Gly Arg Gly Arg Gly Arg Gly Arg Gly Arg Gly Arg Gly Arg
                    100                 105                 110

Gly Arg Gly Gly Pro Arg Arg
            115